United States Patent [19]

Simpson et al.

[11] Patent Number: 4,984,316
[45] Date of Patent: Jan. 15, 1991

[54] BED WARMER

[76] Inventors: Stuart M. Simpson, 86 Beechfield, Leeds, Great Britain, LS12 5OS; Peter Garth, 3 Highwood Avenue, Moortown, Leeds, Great Britain, LS17 6EQ; Jonathan Richards, Polars, High Easter, Chelmsford, Essex, Great Britain, CM1 4RB

[21] Appl. No.: 452,428

[22] Filed: Dec. 19, 1989

[30] Foreign Application Priority Data

Feb. 9, 1989 [GB] United Kingdom ............... 8902879

[51] Int. Cl.⁵ .......................................... A47C 21/04
[52] U.S. Cl. ............................................ 5/508; 5/423
[58] Field of Search .................. 5/423, 421, 482, 469; 62/261; 98/89

[56] References Cited

U.S. PATENT DOCUMENTS

| | | | |
|---|---|---|---|
| 2,093,834 | 9/1937 | Gaugler | 5/423 |
| 2,512,559 | 6/1950 | Williams | 5/423 |
| 3,757,366 | 9/1973 | Sacher | 5/423 |
| 3,778,851 | 12/1973 | Howorth | 5/423 |
| 4,151,658 | 5/1979 | Hibino | 5/508 |
| 4,867,230 | 9/1989 | Voss | 5/469 |

FOREIGN PATENT DOCUMENTS

| | | | |
|---|---|---|---|
| 0113420 | 7/1984 | European Pat. Off. | |
| 716746 | 10/1954 | United Kingdom | 5/423 |
| 783350 | 9/1957 | United Kingdom | |
| 1213123 | 11/1970 | United Kingdom | 5/423 |
| 2022608 | 11/1971 | United Kingdom | 5/469 |

*Primary Examiner*—Alexander Grosz
*Attorney, Agent, or Firm*—Cushman, Darby & Cushman

[57] ABSTRACT

The present invention relates to a generally flat bed warmer which is formed from a flexible, non-porous material. The bed warmer is inserted beneath or between the sheets of a bed for heating up the same. An inlet is defined in the flexible, impervious envelope so that the envelope can be coupled to and inflated by a source of hot air. The heat from the hot air in the bed warmer is transferred to the bed linens through the wall of the envelope. Furthermore, a plurality of apertures are defined through at least one wall of the bed warmer so as to allow controlled leakage of hot air from the bed warmer.

7 Claims, 1 Drawing Sheet

BED WARMER

BACKGROUND OF THE INVENTION

1. Field of the Invention

The present invention relates to bed warmers and, in particular, to a substantially flat bed warmer formed from a flexible material which is adapted to be inserted beneath or between the sheets of a bed and used to heat the sheets and the mattress.

2. Description of the Related Art

To avoid the discomfort of getting in to a cold bed, for centuries various bed warmers have been employed to preheat bed linens. While the forms of bed warmers have changed substantially over the years, the desire to preheat bed linens has never waned.

Most recently, bed warmers have been in the form of hot water bottles and electric blankets. Hot water bottles, however, have the disadvantage that water must be first heated on the stove or hot water must be available from a faucet, the hot water bottle must be filled and then the heavy hot water bottle carried to the bed or the bed linens. All to often, the hot water bottle can become unplugged or otherwise opened, rendering the bed linens unusable. Further, hot water bottles, which are necessarily small because of their weight when filled provide for only very localized heating of bed linens.

Electric blankets have also been used for many years to heat up bed linens and mattresses, as noted above. However, in addition to being relatively expensive, electric blankets lack portability because of their size and thickness and present the risk of electrocution and/or fire as a result of a short or overheating. While electric blanket manufacturers recommend routine servicing to at least minimize the risk of electrocution and/or fire, it is a fact that many electric blankets remain in use even though they are potentially dangerous.

It would therefore be desirable to provide a bed warmer which does not risk soiling the sheets with hot water, and is lightweight and collapsible to a relatively small size so as to be portable and yet expandable to a size large enough to warm a substantial portion of the bed linens. It would further be desirable to provide a bed warmer which can readily heat bed linens to an acceptable and comfortable temperature with safety and in a relatively short period of time.

SUMMARY OF THE INVENTION

The present invention has the object of providing a bed warmer which is relatively inexpensive, expandable to a size which will heat up a substantial portion of a bed and yet compactable to an easily portable state, and which can quickly increase the temperature of the bed linens to a desired temperature.

To achieve the foregoing objects, the present invention is a substantially flat bed warmer made of a flexible material which is capable of being inserted beneath or between the sheets of a bed and of being operated so as to heat up the bed. The bed warmer comprises an inflatable envelope, an inlet communicating with the interior of the envelope for receiving a supply of heated air and at least one aperture air in the form of a hole or an air permeable portion defined in the wall of the envelope to permit controlled leakage of hot air from the envelope upon inflation.

The bed warmer of the invention, then, can be used with any suitable source of heated air at relatively low pressure, above atmospheric. For example, a hair dryer can be employed to fill the envelope with heated air. To fill the envelope, the discharge end of the hair drier, for example, is at least partially inserted into the envelope inlet and operated for five to ten minutes. The envelope is inflated with warm air and the warm air is slowly diffused through the apertures in the envelope into the bed sheets, blankets, and other bed linens. In addition, the mattress and linens are heated by the bed warmer directly through the wall of the envelope.

The bed warmer can be made of any suitable size but is preferably the same area as an electric blanket. Therefore, the bed warmer of the invention is functionally similar to a hot water bottle but heats a much greater area while allowing the bed linens to be brought up to an acceptable temperature quite readily. Once the envelope has become inflated, the further supply of heated air replaces the heat lost through the walls of the envelope and the air which has diffused from the bed warmer to the bed through the apertures. The provision of apertures in the wall of the envelope permit controlled leakage of air from the envelope and into and among the bed clothes, as noted above. This transfer of heated air into the bed clothes and enables the hair dryer or the like to continue to supply heated air to the envelope without risk of overheating as a result of excessive back pressure which otherwise might be generated in a non-perforated envelope.

The envelope is preferably provided with a covering which is compatible with bed linens such as a fibrous material which may be woven or non-woven. In the preferred arrangement, the outer envelope is provided from two sheets of textile material, such as cotton, which are secured together along their peripheral edges by stitching. The inflatable envelope may be made of any suitable flexible material such as a plastic sheet material. The inlet preferably takes the form of an inlet pipe which is sufficiently rigid or arranged with an insert to maintain the inlet in an open condition to facilitate entry of the hair dryer nozzle or the like and inflation of the bed warmer.

A separator or divider sheet may be arranged between the top and bottom plastic sheets of the inflatable envelope so as to prevent adherence of the plastic sheets when the bed warmer is in its collapsed state. The divider sheet may be an air permeable sheet such as a gauze or mesh sheet.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION OF THE PRESENTLY PREFERRED EXEMPLARY EMBODIMENT

Figure 1:
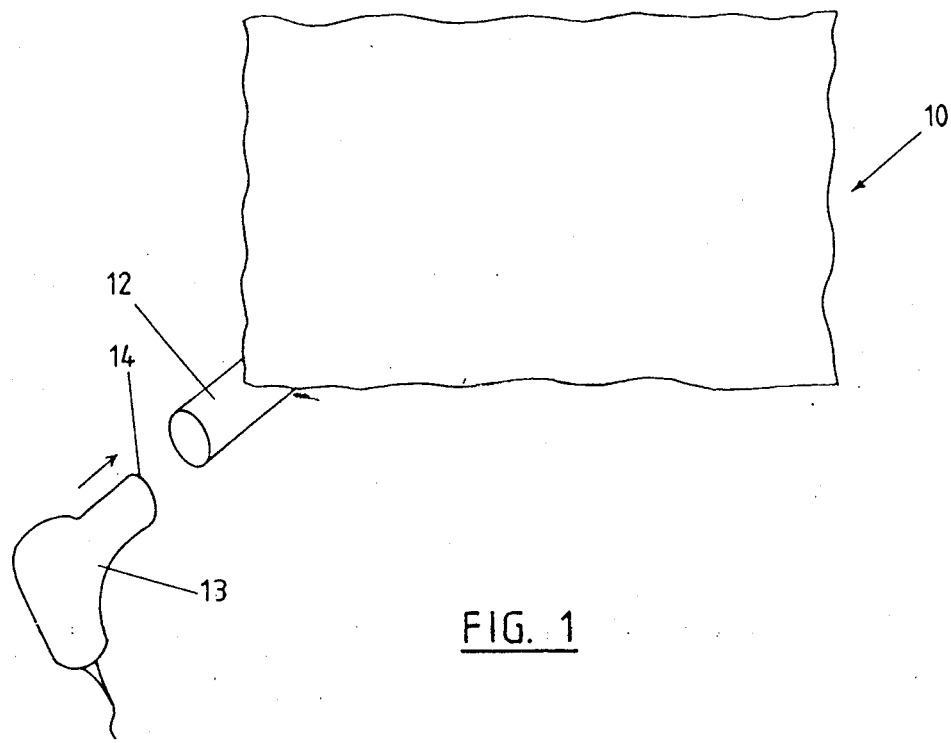
FIG. 1 is a schematic plan view of a substantially flat bed warmer formed from flexible material in accordance with the present invention.

Referring to FIG. 1, the bed warmer provided in accordance with the present invention is shown and designated generally by reference numeral 10. The bed warmer is formed from a flexible material and is intended to be inserted beneath or between the sheets of a bed. Heated air is introduced into the interior of the bed warmer from a source of hot air so that the bed warmer 10 can heat up the bed linens and mattress. Thus, the bed warmer can heat the bed linens and mattress in five to ten minutes. The bed warmer is formed from a relatively flexible material and includes an inner inflatable envelope made up of a substantially impervious material, such as a plastic sheet material. An inlet 12 communicates with the interior of the inflatable envelope 11 and engages an outlet or tube from a supply of hot air. The illustrated embodiment, a hair drier 13 is used to fill the bed warmer by inserting or otherwise coupling discharge nozzle 14 in inlet 12. The hair dryer is then operated for a short period of time to fill the envelope 11 with hot air.

Once the envelope 10 has been inflated with warm air, the heat from the hot air is transferred to the bed linens and mattress (not shown) directly through the wall of the envelope 11. In order to warm a substantial portion of the bed, the bed warmer preferably was dimensions comparable to an electric blanket or the dimensions of the mattress. However, the bed warmer can be provided of any desired size depending upon the size of the bed and area to be warmed thereby. Likewise, while in the illustrated embodiment, the bed warmer is rectilinear. The bed warmer could be of any desired shape such as round, triangular, square, elliptical, etc.

Figure 3:
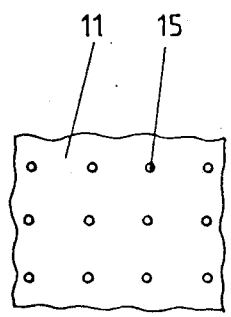
FIG. 3 is a schematic view of a portion of the surface of an inner inflatable envelope of the bed warmer of the invention.

Envelope 11 further includes a number of apertures defined therethrough as shown, in particular, in FIG. 3. While the apertures are in the form of holes in the illustrated embodiment, it is to be understood that the apertures could be in the form of permeable portions of an otherwise impermeable envelope. Thus, in addition to the heat transferred through the wall of the bed warmer to the mattress and sheets, hot air from the interior of the envelope passes through the apertures 15. Thus, controlled leakage of hot air from the envelope upon inflation is permitted. The controlled leakage permits warm air from the envelope to pass into and among the bed cloths. In addition, this controlled leakage allows more hot air to be passed into the impervious envelope from the source of hot air. In this manner, the bed warmer can be periodically refilled or continuously coupled to a source of hot air so that, as the heat from the hot air originally introduced into the bed warmer dissipates, a further supply of heat for warming the bed linens is available.

Figure 2:
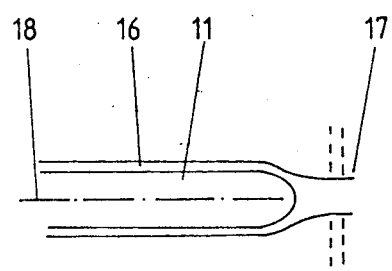
FIG. 2 is a schematic view showing the cross-section of a peripheral portion of the bed warmer of FIG. 1.

A cover is preferably provided for inflatable envelope 11. In the illustrated embodiment, a covering of fibrous material which may be woven or non-woven is formed in surrounding relation to envelope 11. Thus, outer envelope 16 is formed by two sheets of cloth which are stitched together along their peripheral edges as shown in FIG. 2.

Inlet 12 is preferably semi-rigid. Thus, the inlet 12 can be formed form a semi-rigid material or provided with a rigid insert so as to maintain the same in an open condition to facilitate coupling the bed warmer to a source of hot air such as nozzle 14.

While a single inlet 12 is shown in the illustrated embodiment, at one corner of the bed warmer, it is to be understood that the location of the inlet is not critical so long as the inlet projects from the bed warmer in a manner which permits each connection to a hair dryer or other source of heated air. Accordingly, a plurality of inlets can be provided depending upon the size of the bed warmer, air pressure provided by the hot air supply, and desired speed of inflation of the envelope. Furthermore, although not shown, in particular, a plug or cap can be provided for each inlet 12 so that if the source of hot air is detached therefrom, hot air will only escape in a controlled manner through the apertures in the inflated envelope and/or so that only one of several openings can be used without loss of air through another, unused inlet.

As the inner envelope is preferably formed from a flexible plastic material, it is possible that the plastic sheets may adhere to one another when the bed warmer is in its uninflated state and/or folded. Therefore, a separator or divider sheet 18 is preferably disposed within the envelope. The divider sheet 18 can be peripherally coupled to the plastic sheet or simply placed within the envelope. Preferably, the divider is air permeable so as to allow communication between the upper and lower compartments defined thereby. As such, the divider sheet may be a gauze or mesh sheet.

As is apparent from the foregoing, the bed warmer provided in accordance with the present invention can be manufactured more cheaply than an electric blanket but can be operated to bring a substantial portion of the bed linens to a desired temperature safely and in a relatively short period of time.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A bed warmer comprising:
    an envelope formed from a flexible, substantially non-porous material so as to define an air receiving and holding container, said envelope including a top wall and a bottom wall, said walls having a tendency to adhere to each other, and having a substantially flat shape;
    inlet means defined in a wall of said envelope for receiving heated air from a source of hot air to inflate said envelope;
    a plurality of apertures defined through at least one wall of said envelope so as to allow controlled passage of air from the interior of the envelope upon inflation; and
    means for minimizing adherence between said top wall and said bottom wall including a divider sheet disposed within said envelope and extending between and in a plane substantially parallel to said top wall and to said bottom wall of said envelope.

2. A bed warmer as in claim 1, in combination with a cover having a shape substantially corresponding a shape of said envelope and mounted in surrounding relation thereto.

3. A bed warmer as in claim 2, wherein said cover is formed from a porous material so as to allow heated air which passes through said apertures to pass therethrough.

4. A bed warmer as in claim 1, wherein said inlet is defined through a peripheral edge of said envelope.

5. A bed warmer as in claim 1, wherein said envelope is substantially rectilinear.

6. A bed warmer as in claim 5, wherein said inlet is defined at a corner of said rectilinear envelope.

7. A bed warmer as in claim 1, wherein said apertures comprise holes defined through said non-porous material of said envelope.

* * * * *